US011020020B2

(12) United States Patent
Smith et al.

(10) Patent No.: US 11,020,020 B2
(45) Date of Patent: Jun. 1, 2021

(54) VARIABLE VENTILATION AS A DIAGNOSTIC TOOL FOR ASSESSING LUNG MECHANICAL FUNCTION (71) Applicant: UNIVERSITY OF VERMONT AND STATE AGRICULTURAL COLLEGE, Burlington, VT (US)

(72) Inventors: Bradford J. Smith, Burlington, VT (US); Jason H. T. Bates, S. Burlington, VT (US)

(73) Assignee: University of Vermont and State Agricultural College, Burlington, VT (US)

(*) Notice: Subject to any disclaimer, the term of this patent is extended or adjusted under 35 U.S.C. 154(b) by 0 days.

(21) Appl. No.: 15/120,902

(22) PCT Filed: Feb. 23, 2015

(86) PCT No.: PCT/US2015/017132
§ 371 (c)(1),
(2) Date: Aug. 23, 2016

(87) PCT Pub. No.: WO2015/127377
PCT Pub. Date: Aug. 27, 2015

(65) Prior Publication Data
US 2016/0360996 A1  Dec. 15, 2016

Related U.S. Application Data (60) Provisional application No. 61/943,468, filed on Feb. 23, 2014.

(51) Int. Cl.
A61B 5/087  (2006.01)
A61B 5/091  (2006.01)
(Continued)

(52) U.S. Cl.
CPC ............ *A61B 5/087* (2013.01); *A61B 5/0816* (2013.01); *A61B 5/091* (2013.01); *A61B 5/4836* (2013.01);
(Continued)

(58) Field of Classification Search
CPC ....... A61B 5/087; A61B 5/0816; A61B 5/091; A61B 5/4836; A61B 5/7278; A61B 5/7282; A61M 16/0069
(Continued)

(56) References Cited

U.S. PATENT DOCUMENTS 6,254,546 B1    7/2001  Vierto-Oja
8,695,594 B2 *  4/2014  Tham ................. A61M 16/024
                                                 128/204.23
(Continued)

OTHER PUBLICATIONS

Arold, S.P., et al., Variable Tidal Volume Ventilation Improves Lung Mechanics and Gas Exchange in a Rodent Model of Acute Lung Injury, Am. J. Respir. Crit. Care Med., 2002, vol. 165, pp. 366-371. https://www.atsjournals.org/doi/pdf/10.1164/ajrccm.165.3.2010155.
(Continued)

*Primary Examiner* — Navin Natnithithadha
(74) *Attorney, Agent, or Firm* — Hodgson Russ LLP (57) ABSTRACT Systems and methods for determining lung recruitment/derecruitment dynamics of an individual are disclosed. The disclosed embodiments advantageously use variable ventilation of the individual to determine lung dynamics without necessitating additional, potentially harmful ventilation maneuvers.

11 Claims, 8 Drawing Sheets (51) Int. Cl.
*A61B 5/00* (2006.01)
*A61B 5/08* (2006.01)
*A61M 16/00* (2006.01)

(52) U.S. Cl.
CPC .......... *A61B 5/7278* (2013.01); *A61B 5/7282* (2013.01); *A61M 16/0069* (2014.02)

(58) Field of Classification Search
USPC ................................................ 600/529–538
See application file for complete search history.

(56) References Cited

U.S. PATENT DOCUMENTS

| | | | | |
|---|---|---|---|---|
| 8,973,578 B2* | 3/2015 | Dellaca' | ........... | A61M 16/0051 128/204.18 |
| 2008/0072896 A1 | 3/2008 | Setzer et al. | | |
| 2008/0295839 A1* | 12/2008 | Habashi | ............ | A61M 16/0051 128/204.22 |
| 2009/0272381 A1 | 11/2009 | Dellaca et al. | | |
| 2012/0266882 A1* | 10/2012 | Dellaca | ............. | A61M 16/0051 128/204.23 |
| 2015/0068526 A1* | 3/2015 | Habashi | ............ | A61M 16/0051 128/204.22 |
| 2015/0289785 A1* | 10/2015 | Bojovic | ................ | A61B 5/091 600/534 |

OTHER PUBLICATIONS

Mutch, W.A.C., et al., Biologically Variable or Naturally Noisy Mechanical Ventilation Recruits Atelectatic Lung, American Journal of Respiratory and Critical Care Medicine, 2000, vol. 162, No. 1, pp. 319-323. http://www.atsjournals.org/doi/abs/10.1164/ajrccm.162.1.9903120.

* cited by examiner

Fig. 11

VARIABLE VENTILATION AS A DIAGNOSTIC TOOL FOR ASSESSING LUNG MECHANICAL FUNCTION

CROSS-REFERENCE TO RELATED APPLICATIONS

This application claims priority to the provisional patent application titled "Variable Ventilation as a Diagnostic Tool for Assessing Lung Mechanical Function," filed Feb. 23, 2014 and assigned U.S. App. No. 61/943,468, the disclosure of which is hereby incorporated by reference.

STATEMENT REGARDING FEDERALLY SPONSORED RESEARCH OR DEVELOPMENT

This invention was made with government support under P30 GM103532 and T32 HL0 076122 awarded by the National Institutes of Health. The government has certain rights in the invention.

FIELD OF THE INVENTION

This invention relates to lung diagnostics and, more particularly, to variable ventilation as a lung diagnostic.

BACKGROUND OF THE INVENTION

Acute respiratory distress syndrome (ARDS) is a sudden failure of the respiratory system that deprives organs of necessary oxygen. ARDS can be caused by injury to the lungs such as, for example, aspiration, chemical inhalation, pneumonia, septic shock, or trauma. Fluids may build up in the air sacs (alveoli), which decreases the lung's ability to expand and prevents oxygen from passing into the bloodstream. ARDS is a life-threatening condition that usually requires hospitalization. There are currently no pharmaceuticals or other therapies that have been proven efficacious in ARDS, so treatment may entail only supportive care using mechanical ventilation. Of the approximately 200,000 patients diagnosed with ARDS each year in the United States, approximately 75,000 will be overwhelmed by their own biologic response to the lung injury. In a severe form, ARDS has a mortality of approximately 30% to 40%. Ventilator-induced lung injury (VILI), or the stress or strain applied to the lung during mechanical ventilation, can further damage already injured lung tissue and further contribute to ARDS mortality.

The current standard of care for ARDS dictates use of mechanical ventilation with a low tidal volume ($V_t$) of 6 ml/kg ideal body weight to reduce VILI caused by over-distention (volutrauma) together with positive end-expiratory pressure (PEEP) to maintain airway patency or use of prone positioning. These guidelines are based on the aggregate characteristics of ARDS patients in general, which constitute a rather heterogeneous patient population in which the best average strategy is may not be best in any particular case. Therefore, optimizing mechanical ventilation for individual patients should improve outcomes beyond the current universally applied low-$V_t$ approach. However, personalized management of mechanical ventilation advantageously involves the minimization of a cost function describing the injury that different ventilatory settings would cause. Any such injury prediction may depend on the current injury status of the lung, and thus may need to be based on diagnostic parameters that can be tracked continuously over time.

Such diagnostic parameters may relate to lung mechanical function, since it has been shown that acute lung injury is typically accompanied by substantial changes in lung derecruitability, reflected in the propensity of a recruited lung to derecruit over time. Assessing the derecruitability of an individual's lungs may require that lung volume be periodically perturbed in a manner sufficient to cause a significant degree of recruitment, so that the dynamics of subsequent derecruitment can be observed. This has been previously achieved in mouse models of lung injury by recruiting the lungs with a large inspiration and then tracking lung elastance while low-$V_t$ ventilation is applied at various levels of PEEP. This provides a set of elastance time profiles to which can be fit to a computational model that recapitulates the regionally distributed time-dependent nature of derecruitment. Previous in vitro and computational studies suggest that this model can be used to infer the extent to which lung injury affects surface tension at the air-liquid interface. However, the ventilatory maneuvers employed in mice to determine derecruitability do not resemble any of the conventional regimens of mechanical ventilation employed for managing ARDS patients, and thus are very unlikely to be considered clinically acceptable methodologies by the medical community.

Because of the ever present risk of VILI, mechanical ventilation requires balancing the provision of life giving ventilation against the delivery of injurious stresses and strains to the tissue. Of these two competing factors, reducing the stresses and strains on the lung tissues is paramount. In fact, the only evidence-based intervention so far shown to reduce mortality in ARDS is the reduction of tissue strain through the use of low tidal volumes, even when this causes $CO_2$ to rise to levels that are much higher than normal. Similarly, it is standard practice to apply some level of PEEP to the injured lung in an attempt to mitigate the damaging stresses caused by repetitive re-opening of lung units that derecruit during each expiration.

Nevertheless, it may not always be possible to prevent VILI entirely, so the goal of mechanical ventilation may be to minimize the rate at which VILI develops, in the hope that the body will eventually recover on its own. Currently, the factors that minimize the progression of VILI are only generally understood, and there are no ventilatory regimes that are optimally-designed. The situation is complicated by the fact that adequate ventilation can be provided to the lungs in an essentially limitless range of configurations, each defined by a particular combination of $V_t$, PEEP, and depth and frequency of recruitment maneuvers. However, these configurations are not all equal in their capacities to damage the lungs. Consequently, there is a pressing need for a method of predicting how much VILI would be produced in a given lung by a given regimen of mechanical ventilation. Future injury is strongly determined by existing injury, so a method for assessing the injury status of the lung that can be applied rapidly and continually is needed. Furthermore, a method of mechanical ventilation for ARDS that can be tailored to suit the pathophysiological characteristics of individual patients is needed. This would be able to personalize mechanical ventilation in a manner that is more optimal in the sense of being minimally injurious.

BRIEF SUMMARY OF THE INVENTION

Variable ventilation (VV) is a new mode of mechanical ventilation in which tidal volume and breathing frequency vary randomly from breath to breath, and is motivated by the fact that natural breathing is also variable rather than completely regular. VV has been shown to be efficacious relative to regular mechanical ventilation in animal models of lung disease, and is now entering human trials. VV can be advantageously used as a diagnostic tool whereby the variable perturbations in lung volume applied by VV are used to determine the dynamic mechanical properties of the lung, providing critical information about how best to manage ARDS.

Assessing how easily and rapidly the injured lung derecruits (progressively collapses) over time is not currently done clinically, but this assessment is readily performed in patients receiving variable ventilation and can be used for managing patients with ARDS. Embodiments disclosed herein may be used to address this clinical need.

A method of mechanical ventilation may assess the injury status of a lung, predict how much VILI will be caused in that lung by a given regimen of mechanical ventilation, and optimize ventilation to be minimally injurious based on the information from the assessment and prediction. These three steps may be cycled through continuously.

The disclosed methods also may perturb lung volume in a manner that will be safe for ARDS patients while at the same time allowing the dynamics of recruitment and derecruitment (R/D) to be observed.

Testing was performed on synthetic pressure and flow data generated with established numerical models of lung function corresponding to both healthy mice and mice with lung injury. The data were generated by subjecting the models to a variety of mechanical ventilation regimens including variable ventilation. Results support the hypothesis that variable ventilation can be used as a diagnostic tool to identify the injury status of the lung in ARDS.

In a first embodiment, a method for measuring lung function of an individual being mechanically ventilated with a ventilator is provided. Using a ventilator, breath cycles are supplied to the individual. The breath cycles have varying tidal volumes such that at least one of the breath cycles does not have a same tidal volume as at least one of the other breath cycles. Airway pressure and airway flow (i.e., rate of flow) are measured during the breathing cycles. Lung derecruitability is determined from the airway pressure measurements and airway flow measurements.

A mean tidal volume of the plurality of breath cycles is $Vt_{Mean}$. The tidal volumes of the breath cycles can vary from $0.7Vt_{Mean}$ to $2.25Vt_{Mean}$ or from $0.7 Vt_{Mean}$ to $3.5Vt_{Mean}$. The tidal volumes can be distributed according to a specified probability distribution function. For example, the tidal volumes can be distributed according to a Gaussian function.

In a second embodiment, an apparatus for determining a lung function of individual being ventilated by a ventilator is provided. The ventilator is configured to provide variable ventilation to the individual through an airway. The apparatus includes a processor and an airway meter in communication with the processor. The airway meter is configured to measure a pressure and flow of the airway. The processor is programmed to receive measurements of airway pressures and airway flows from the airway meter and determine lung derecruitability from the airway pressure and airway flow measurements. The apparatus also may include an interface in communication with the processor. The interface is configured to communicate with the ventilator. The processor can be further programmed to utilize data received from the ventilator in determining lung derecruitability.

In a third embodiment, an apparatus for determining a lung function of individual is provided. The apparatus includes a ventilator, an airway meter, and a processor. The ventilator is configured to provide variable ventilation to the individual through an airway. The airway meter is configured to measure a pressure and flow of the airway. The processor is programmed to receive measurements of the airway pressures and airway flows from the airway meter, receive data from the ventilator, and determine lung derecruitability from the airway pressure measurements, airway flow measurements, and ventilator data.

DESCRIPTION OF THE DRAWINGS

For a fuller understanding of the nature and objects of the invention, reference should be made to the following detailed description taken in conjunction with the accompanying drawings, in which.

DETAILED DESCRIPTION OF THE INVENTION

Although claimed subject matter will be described in terms of certain embodiments, other embodiments, including embodiments that do not provide all of the benefits and features set forth herein, are also within the scope of this disclosure. Various structural, logical, process step, and electronic changes may be made without departing from the scope of the disclosure.

Figure 11:
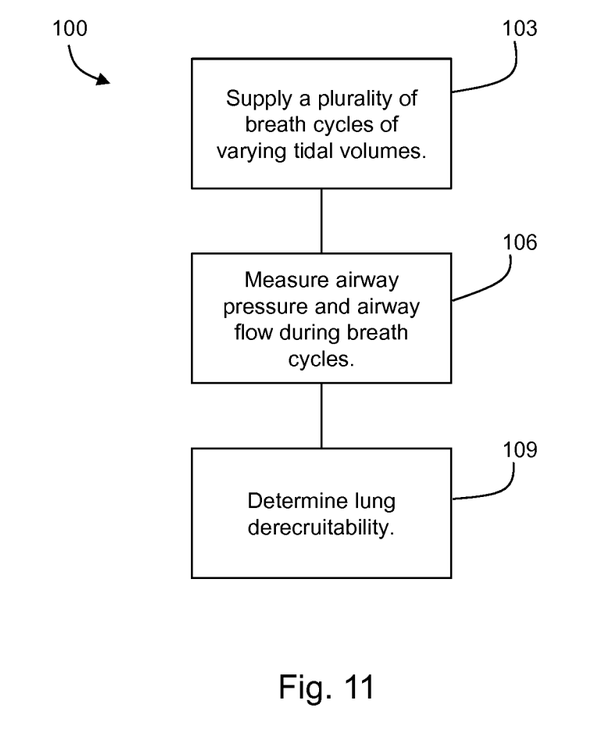
FIG. 11 is a flowchart of a method according to an embodiment of the present disclosure.

The present disclosure may be embodied as a method 100 for characterizing lung function of an individual being mechanically ventilated with a ventilator (see, e.g., FIG. 11). A ventilator is used to supply 103 a plurality of breath cycles (cycles of inspiration and expiration) to the individual. The provided ventilation is "variable ventilation" where the breath cycles have varying tidal volumes. In this way, at least one of the plurality of breath cycles does not have a same tidal volume as at least one of the other breath cycles of the plurality. The supplied 103 breath cycles may have a mean tidal volume, $Vt_{Mean}$. In one embodiment, the breath cycles of the supplied 103 plurality of breath cycles vary from a low tidal volume to a high tidal volume. For example, the low tidal volume may be $0.6Vt_{Mean}$, $0.7Vt_{Mean}$, $0.8Vt_{Mean}$, or any other value determined to be beneficial in implementing the disclosed method for an individual. The high tidal volume may be, for example, $2.0Vt_{Mean}$, $2.25Vt_{Mean}$, $2.5Vt_{Mean}$, or any other value for an individual. The low and high values may be selected based on the individual, the injury of the individual, or otherwise. For example, tidal volumes as high as $3.5Vt_{Mean}$ or higher may be used where the lungs are relatively healthy. The varying volumes of the breath cycles may be distributed across the range in a specified probability distribution function or, for example, a Gaussian distribution.

The method 100 further comprises measuring 106 the airway pressure and airway flow during the breath cycles. The lung function of the individual is characterized by determining 109 lung derecruitability as is further described below under the section heading "Discussion."

Figure 10:
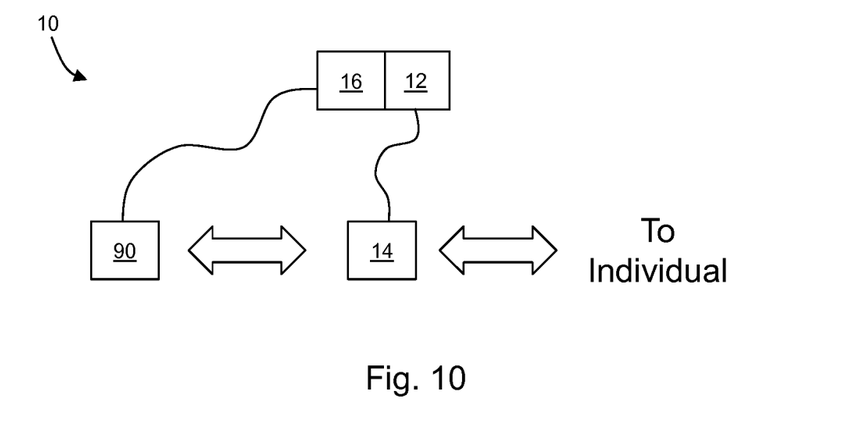
FIG. 10 depicts an apparatus according to an embodiment of the present disclosure.

The present disclosure may be embodied as an apparatus 10 for characterizing a lung function of individual being ventilated by a ventilator 90 using variable breath tidal volumes (i.e., variable ventilation). The apparatus 10 comprises a processor 12 and an airway meter 14 in communication with the processor 12. The airway meter 14 is configured to measure pressure and flow within an airway between the ventilator 90 and the individual and supply such measurements to the processor 12. The airway meter 14 may comprise sensors for use in an existing airway (e.g., sensors that can be utilized in the tubing of the ventilator). In another example, the airway meter 14 may be configured as an adapter for insertion in the pneumatic pathway between the ventilator 90 and the individual. Other airway meter 14 configurations will be apparent in light of the present disclosure. The apparatus 10 may further comprise an interface 16 configured to communicate with the ventilator. For example, the interface 16 may be a serial data port, a wireless device, or any other technique for interfacing the apparatus 10 with the ventilator 90.

The processor 12 is programmed to receive a plurality of measurements of airway pressures and flows form the airway meter 14. Such measurements are taken, for example, during the varying breath cycles provided to the individual by the ventilator 90. The processor 12 is further programmed to determine lung derecruitability from the airway pressure measurements and airway flow measurements as further described below under the heading "Discussion." Where an interface 16 is provided, the processor 12 may be further programmed to utilize data received from the ventilator in determining lung derecruitability.

In another embodiment, an apparatus 20 is provided which is similar to the above-described embodiment (apparatus 10), and additionally comprises the ventilator 90.

Discussion

The objectives of being able to perturb lung volume in a manner safe for ARDS patients while allowing the dynamics of R/D to be observed may be met by VV, which attempts to recapitulate the breath-to-breath changes in $V_t$ and breathing frequency seen during spontaneous breathing. VV has been shown to be protective in animal models of lung injury, and it has been previously shown that this therapeutic efficacy may be related to the dynamics of R/D.

VV also can be used as a diagnostic modality that provides the volume perturbations necessary to identify lung derecruitability. Derecruitability can be estimated from synthetic airway pressure and flow data generated by subjecting a computational model of R/D dynamics to regimens of VV.

Pressure and flow can be simulated at the airway opening during mechanical ventilation using a simulation model having $N_{Units}$=48,000 parallel elastic lung units. Each lung unit had an elastance $E_{Unit}$ that was constant at low volumes but which increased quadratically with volume above a critical volume $V_{Crit}$ thus:

$$E_{Unit}(V_{Unit}) = N_{Units} \begin{cases} E_{Base}, & \text{if } V_{Unit} \leq V_{Crit}/N_{Units} \\ E_{Base} + E_{Fac}((V_{Crit}/N_{Units})/N_{Units})^2, & \text{if } V_{Unit} > V_{Crit}/N_{Units} \end{cases} \quad (1)$$

where $E_{Base}$, $E_{Fac}$ (=$13E_{Base}$), $V_{Unit}$ are constants. The elastance $E_{mod}$ of the entire model was a function of the number of open units $N_{Open}$ according to $$E_{Mod}(t) = \left[ \sum_{i=1}^{N_{Units}} \begin{cases} 0 & \text{closed unit} \\ 1/E^i_{Unit}(V^i_{Unit}) & \text{open unit} \end{cases} \right]^{-1} \quad (2)$$

The airflow resistance of each unit was $R_{unit}=N_{Units}R_{aw}$, with $R_{aw}$=0.47 cmH$_2$O·s·ml$^{-1}$ to match experimental observations. The total resistance $R_{mod}$ of the model was therefore $$R_{mod}(t) = R_{Unit}[N_{Open}(t)]^{-1} \quad (3)$$

Flow into the model for each breath was driven by a volume waveform buffered by a gas elastance $E_{gas}$=130 cmH$_2$O·ml$^{-1}$, representing the ventilation delivered by a small animal ventilator. Inspiration was sinusoidal, while expiration from the model was driven by the difference between the elastic recoil pressure within each open lung unit and the prescribed level of PEEP. The rate of expiration from each unit was governed by the ratio of this pressure difference to the sum of $R_{Unit}$ and the resistance of the ventilator tubing $R_{eq}$=0.4 cmH$_2$O·s·ml$^{-1}$.

Nomenclature is listed in Table I.

TABLE I

Nomenclature

| Parameter | Description |
|---|---|
| $N_{Units}$ | Number of respiratory units |
| $N_{Open}$ | Number of open units |
| $V_{Unit}$ | Respiratory unit volume |
| $E_{Unit}$ | Respiratory unit (RU) Elastance |
| $E_{Base}$ | Low-volume elastance |
| $E_{Fac}$ | Elastance increase rate in nonlinear regime |
| $V_{Crit}$ | RU transition volume between linear and nonlinear elastance |
| $E_{mod}$ | Total model elastance |
| $R_{mod}$ | Total model resistance |
| $R_{Unit}$ | Unit resistance |
| y | Virtual trajectory |
| $S_C$ | Virtual trajectory closing velocity constant |
| $\lambda_C$ | Constant which defines exponential PDF for $S_C$ |
| $S_O$ | Virtual trajectory opening velocity constant |
| $P_C$ | Virtual trajectory closing pressure |
| $P_O$ | Virtual trajectory opening pressure |
| μ | Mean virtual trajectory closing pressure |
| ΔP | Difference between $P_C$ and $P_O$ |
| P | Airway pressure |
| $V_t$ | Ventilation tidal volume |
| α | Closing pressure distribution weighting vector |
| λ | Vector of closing velocity constant PDFs [$\lambda_C$] |
| Variable Ventilation Parameters | |
| $p(V_t)$ | Volume PDF for VV |
| $g_0$ | VV normalization constant |
| $Vt_{Mean}$ | VV mean tidal volume |
| $Vt_{Min}$ | VV minimum tidal volume |
| $V_{Max}$ | VV maximum tidal volume |
| $V_P$ | Peak $V_t$ for uniform portion of VV PDF |
| δ | VV decay constant |
| Pattern Search Algorithm Parameters | |
| $n_{param}$ | Number of parameters to fit with PPS |
| $n_g$ | Number of possible values for each fit parameter |
| $p_{max}$ | Maximum number of search directions |
| l | Lower bound of parameter space |
| u | Upper bound of parameter space |
| k | Pattern search algorithm iteration number |
| $x_k$ | $k^{th}$ vector of best-fit parameters |
| $\Delta_k$ | $k^{th}$ step size vector |
| D | Set of search directions for PPS |
| $d^{(i)}$ | $i^{th}$ search direction vector of length $n_{param}$ |
| $p_{max}$ | Maximum number of search directions |
| $X_k$ | Set of trial points for the $k^{th}$ PPS search step |
| Analysis Parameters | |
| $\varphi_S$ | Respiratory unit open fraction for simulation model |
| $\varphi_E$ | Respiratory unit open fraction for estimation model |
| K | Composite $P_C$ PDF in the simulation model |
| $\kappa_i$ | $i^{th}$ of the four $P_C$ PDFs in the estimation model |
| $\varepsilon_P$ | Error in the $P_C$ PDFs between simulation and estimation models |
| $\varepsilon_E$ | Error in elastance between estimation and simulation models |

The dynamics of R/D of each lung unit was simulated using virtual trajectories which provide an empirical approximation to the pressure dependence and latency of these phenomena. Each lung unit was associated with a trajectory represented by a variable 0≤y≤1 that decreased in value at a rate given by $dy/dt=S_C(P-P_C)$ if the airway pressure P was less than the critical closing pressure $P_C$; $S_C$ is the closing velocity constant. Conversely, if P was greater than the critical opening pressure $P_O$ then $dy/dt=S_O(P-P_O)$. The opening velocity constant $S_O$=10$S_C$, causing reopening to occur an order of magnitude more quickly than closure, as is the case in injured mice. The model equations were integrated using the forward Euler method at a simulation frequency of 150 Hz.

The dynamics of the model were thus governed by statistical distributions used to assign values of $P_O$, $S_O$, $P_C$ and $S_C$ to each lung unit. Closing and opening pressures have previously been reported to follow Gaussian distributions, and we have used these distributions in previous model fitting studies. Accordingly, $P_C$ in the present study was drawn from a Gaussian distribution having a mean μ specified to correspond to a particular clinical situation. The standard deviation of the Gaussian was 3 cm H$_2$O in all cases. $P_O$ was also drawn from a Gaussian distribution such that $P_O=P_C+\Delta P$ with ΔP=4 cm H$_2$O in all cases. We have also found in previous model fitting studies that monotonically decreasing probability distribution functions (PDFs) are appropriate for $S_O$ and $S_C$, so in the present study we selected these parameters from exponential PDFs.

The simulation model can be initialized by ventilating it for 1 min with $V_t$=0.25 ml at 200 breaths/min followed by two deep inspirations (DI, $V_t$=1.0 ml, 0.8 Hz). This ventilation sequence was applied to provide a standardized volume history for the virtual trajectories for each iteration of the model, and the two large DIs were included to fully recruit the simulation model.

Eighty second sequences of mechanical ventilation were then applied at a respiratory rate of 240 breaths/min (appropriate for a 20 g mouse) in the four patterns listed below. The first 40 seconds were used to establish a standardized volume history, while the pressures and flows in the later 40 seconds (the fitting period) were used to estimate derecruitability as described in below.

VV$_H$: VV for healthy mice. The tidal volume of each breath was chosen using the probability density function defined by $$p(V_t) = \begin{cases} g_0 & \text{for } Vt_{Min} \leq V_t \leq V_P \\ g_0(V_t/V_P)^{-\delta} & \text{for } V_P \leq V_t \leq V_{Max} \end{cases} \quad (4)$$

where $Vt_{Mean}$ is mean tidal volume (8.0 ml/kg), $Vt_{Min}$ is the minimum tidal volume (0.7$Vt_{Mean}$), $V_{Max}$ is maximum tidal volume (3.5$Vt_{Mean}$), $V_P$=0.9$Vt_{Mean}$, the decay constant δ=5.1, and PEEP=3 cm H$_2$O. The normalization constant $g_0$=3.35 was chosen so that $\int_{Vt_{Min}}^{V_{Max}} p(V_t)dV_t=1$.

VV$_I$: VV for mice with HCl-induced lung injury. This was identical to VV$_H$ except with $V_{Max}$=2.25$Vt_{Mean}$ and $g_0$=3.31.

CV: Constant volume ventilation with $V_t$=8.0 ml/kg and PEEP=3 cm H$_2$O.

CV-RM: Constant volume ventilation with $V_t$=8.0 ml/kg and PEEP=3 cm H$_2$O with two successive 50 ml/kg inspirations at 0.8 Hz applied at the onset of the fitting period.

Table II lists parameter values for healthy mice.

TABLE II

Parameter Values for Healthy and Injured Mice

| Variable | Healthy Mouse | VILI Mouse |
|---|---|---|
| $E_{Base}$ (cm H$_2$O) | 11.5 | 14 |
| $V_{Crit}$ (ml) | 0.6 | 0.55 |
| RU Group 1 Membership | 100% | 30% |
| RU Group 1 μ (cm H$_2$O) | 0 | 3 |
| RU Group 1 $\lambda_C$ | 4 | 4 |
| RU Group 2 Membership | 0% | 70% |
| RU Group 2 μ (cm H$_2$O) | N/A | 18 |
| RU Group 1 $\lambda_C$ | N/A | 0.5 |

Figure 3:
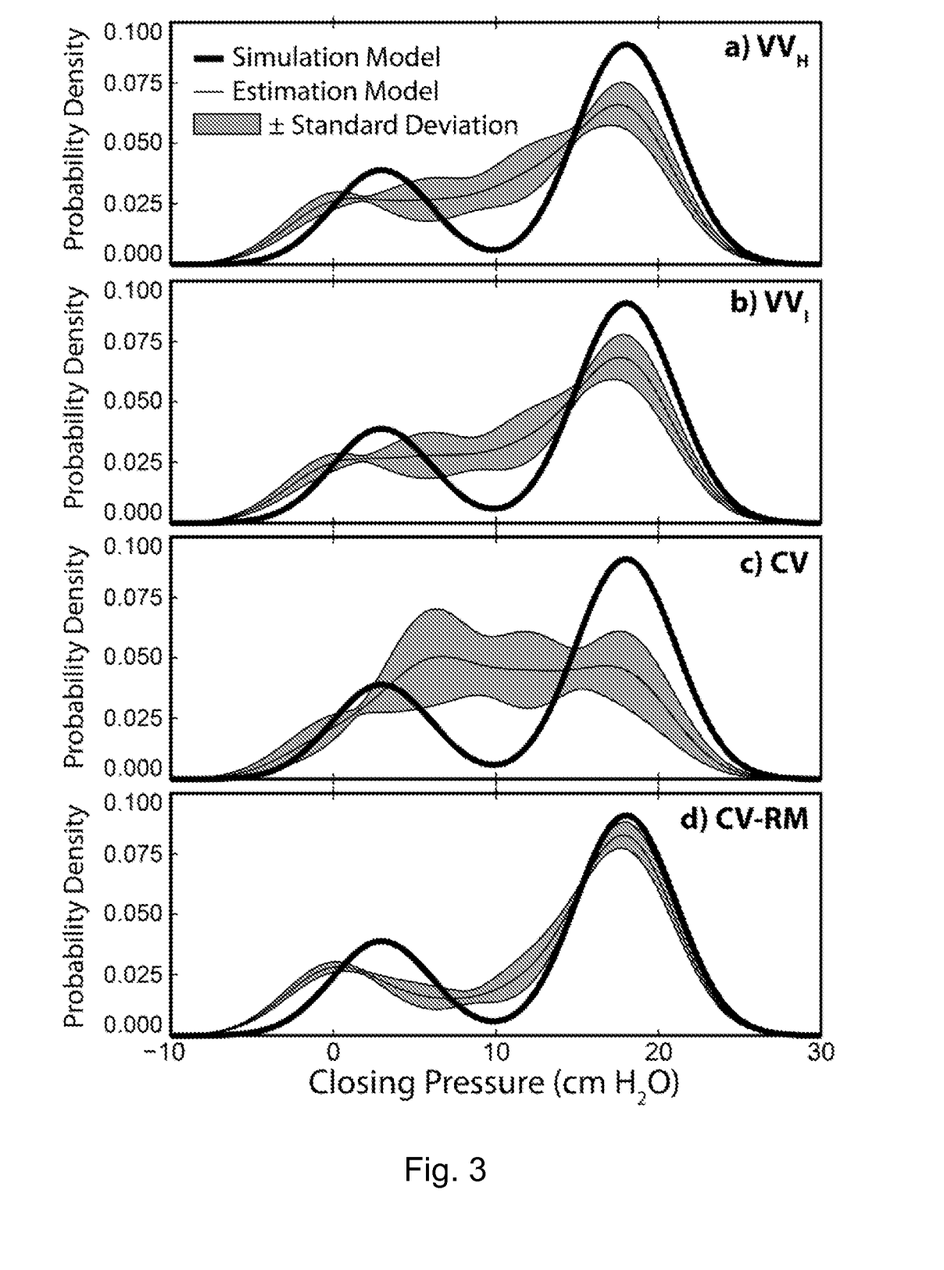
FIG. 3 plots probability density of the closing pressure for injured mice prescribed in the simulation model (black line) and computed using the estimation model wherein gray area shows the mean±standard deviation of 16 iterations of the estimation model.

Pressure and flow were simulated at the airway opening during VVH, VVI, CV, and CV-RM in a healthy BALB/c mouse and a mouse with VILI to enable calibration of the model to previously collected experimental data. The model parameters for these two conditions are listed in Table II. The progression of VILI is accompanied by changes in lung derecruitability that can be characterized in terms of two injury-dependent populations of lung units with markedly different R/D characteristics. Accordingly, the lung units in the VILI simulations were separated into two groups, one containing 30% of the units that opened and closed relatively slowly with low critical opening and closing pressures, and the remaining 70% that opened and closed more rapidly at higher pressures (Table II). This gave bimodal PDFs for $P_O$ and $P_C$ for the injured mice as shown in FIG. 3 (black line). These $P_C$ PDFs are similar to the distributions of regional compliance at low inflation pressures in dogs with oleic acid injury, suggesting that acid injury increased $P_C$ in a subset of lung units resulting in derecruitment and decreased compliance. Furthermore, at higher inflation pressures the compliance distributions were similar to those of healthy dogs. This indicates that recruitment in the injured lung occurred between 15 and 20 cm $H_2O$ which is in agreement with the 18 cm $H_2O$ upper peak of our bimodal $P_C$ distribution.

B. Estimation of Lung Derecruitability

Lung derecruitability was estimated from the simulated airway pressure and flow data generated by the simulation model using an estimation model that was similar in many ways to the simulation model but significantly simpler in structure so that its parameters could be determined uniquely by model fitting. The estimation model contained $N_{Units}=512$ lung units. The PDF for $P_C$ in the estimation model comprised the superposition of four Gaussian distributions having means at 0, 6, 12, and 18 cm $H_2O$ each with a standard deviation of 3 cm $H_2O$. The amplitudes of these four Gaussians were specified by a weighting vector $\alpha=[\alpha_1, \alpha_2, \alpha_3, \alpha_4]$. Similarly, PDFs for $S_C$ for each of these four Gaussian $P_C$ distributions were chosen from exponential distributions of the form $\lambda_c e^{-\lambda_c z}$, where the value of $\lambda_c$ for each distribution was specified in the four element vector $\lambda$.

Table III lists initial conditions.

TABLE III

Initial Conditions

| Variable | Lower Bound (l) | Upper Bound (u) | Initial Step Size ($\Delta_0$) | Mean Starting Value ($x_0^{mean}$) |
|---|---|---|---|---|
| $E_{Base}$ | 8 | 18 | 1.5 | 15 |
| $V_{Crit}$ | 0.4 | 0.7 | 0.05 | 0.575 |
| $\alpha$ [1-4] | 0.0 | 1.0 | 0.125 | [1.0, 0.1, 0.1, 0.1] |
| $\lambda$ [1-4] | 0.025 | 2.5 | 1 | 0.8 |

To fit the estimation model to data generated by the simulation model, $n_{param}=10$ parameters that together minimized the objective function $f=RMS(P_{sim}-P_{est})$ when the estimation model was driven by the corresponding ventilation waveform was determined. Here, $P_{sim}$ and $P_{est}$ are the airway pressures predicted by the simulation and estimation models, respectively, and RMS indicates the root mean square. The parameters are the four components of $\alpha$, the four components of $\lambda$, $E_{Base}$ and $V_{Crit}$ (Table III). Model fitting was achieved iteratively using a constrained parallel pattern search (PPS) algorithm that functions by repeatedly simulating pressure and flow data with the estimation model using sets of parameter values selected from within a specified bounded domain. The lower (l) and upper (u) bounds on this domain, listed in Table III, were selected to include parameter values that were observed in previous experimental studies in mice. To standardize the volume history of the estimation model prior to each run through the iterative fitting algorithm a first 40-second period of ventilation was applied using the prescribed ventilation pattern. A second 40-second period of ventilation was then applied and these data were used to compute the value of the objective function.

The initial guess for the parameter values was $x_0=x_0^{mean}+\Delta_0 B$ where $x_0^{mean}$ is the average parameter starting value (Table III), B is a random number from a uniform distribution $-1 \leq B \leq 1$, and $\Delta_0$ is the initial step size vector. This random variation was included to avoid bias in the solution due to the prescribed initial conditions which would be unknown in clinical or laboratory scenarios.

A set of search directions $\mathcal{D}=\{d^{(1)}, \ldots, d^{(P_{max})}\}$ was defined where each $d^{(i)}$ is a vector of length $n_{param}$. Superscripts indicate the direction index, the maximum number of search directions $p_{max}=n_g^{n_{param}}=59049$, and $n_g=3$ is the number of possible values for each variable in x. The search directions were defined as $$d^{(i)}(j) = \left\lfloor \frac{i}{n_g^j} \right\rfloor - n_g \left\lfloor \left\lfloor \frac{i}{n_g^j} \right\rfloor / n_g \right\rfloor - 1 \qquad (5)$$

$$0 \leq i < p_{max} \text{ and } 0 \leq j < n_{param}$$

Each iteration of the pattern search algorithm $0 \leq k \leq 30$ comprised three steps:

First, generate a set of trial points which correspond to the search directions $$X_k^{(i)} = \{x_k + \Delta_k d^{(i)} : 0 \leq i \leq p_{max}\} \qquad (6)$$

where $\Delta_k$ is the step size vector and $x_k$ is the solution vector from the previous step. The four (out of $n_{param}$) elements for each $X_k^{(i)}$ corresponding to the weighting vector $\alpha$ are scaled to a magnitude of 1 and duplicate trial points resulting from this transformation are removed. Likewise, any direction index which contains points outside the constrained domain $l \leq X_k^{(i)} \leq u$ is also eliminated. Finally, only a single value of $\lambda_c$ is included for any entry of $\alpha=0$, where the remainder of the trial parameter values are identical. The remaining trial points in $X_k$ are evaluated in a queue.

Second, if a trial point $z_k \in X_k$ exists so that $f(z_k)<f(x_k)$ then the iteration is deemed successful, and we set $x_{k+1}=z_k$, $\Delta_{k+1}=\Delta_k$, and return to step 1 if $k \leq 30$. Otherwise, the algorithm is terminated.

Third, if a trial point $z_k \in X_k$ does not exist so that $f(z_k)<f(x_k)$ then the iteration is deemed unsuccessful and $x_{k+1}=x_k$ was set and $\Delta_{k+1}=0.5\Delta_k$. If $k \leq 30$ and $\Delta_{k+1}>0.025\Delta_0$ the algorithm returns to step 1. Otherwise, the algorithm is terminated.

The pattern search algorithm is readily parallelized because once $X_k$ is calculated the objective function evaluation for each trial point is independent of the others. Accordingly, the above algorithm was implemented using the compute unified device architecture on a graphics processing unit (GPU) (Tesla K20, NVIDIA, Santa Clara Calif.). Each trial point was assigned to an independent thread on the GPU and dynamic parallelism was used to branch each trial point into 512 additional threads (1 per RU) which were then used to evaluate the dynamics of R/D. This approach provided a substantial performance improvement, particularly when polling smaller parameter spaces near the bounds of the search domain.

Figure 1:
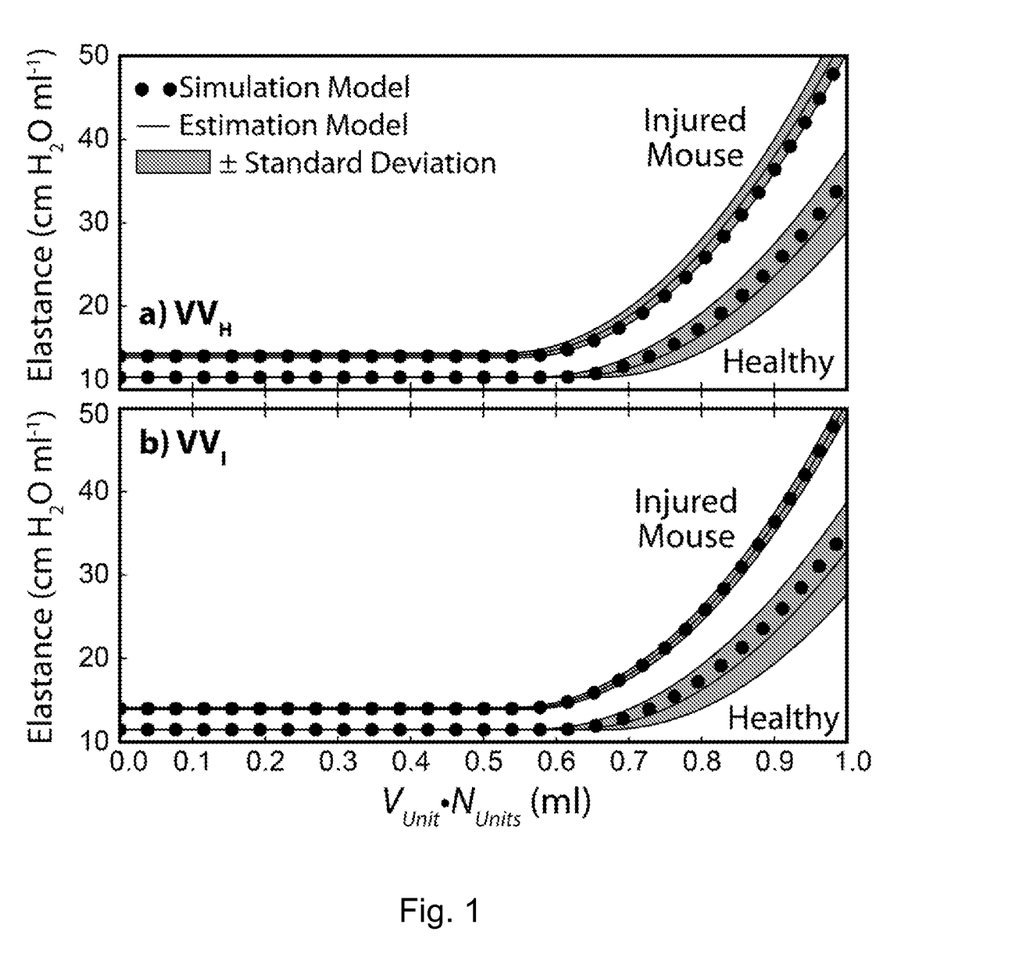
FIG. 1 compares lung unit elastance prescribed in the simulation model (black circles) and determined with the estimation model using $VV_H$ (a) and $VV_I$ (b) for healthy and injured mice wherein the shaded area shows mean±standard deviation over 16 runs.

FIG. 1 shows $E_{Unit}$ as a function of total lung volume in the fully recruited lung for the healthy and injured simulation models (circles), as well as the corresponding $E_{Unit}$ curves for selected cases provided by the estimation model (the latter are the averages of 16 estimations obtained using different random initial guesses for the parameter values of the estimation model). The gray areas in FIG. 1 show the mean±standard deviation, demonstrating the repeatability of these estimates. These results show that the volume dependence of $E_{Unit}$ can be accurately estimated from the airway pressure and flow data recorded during various modes of mechanical ventilation in mice, including two different types of VV.

Figure 2:
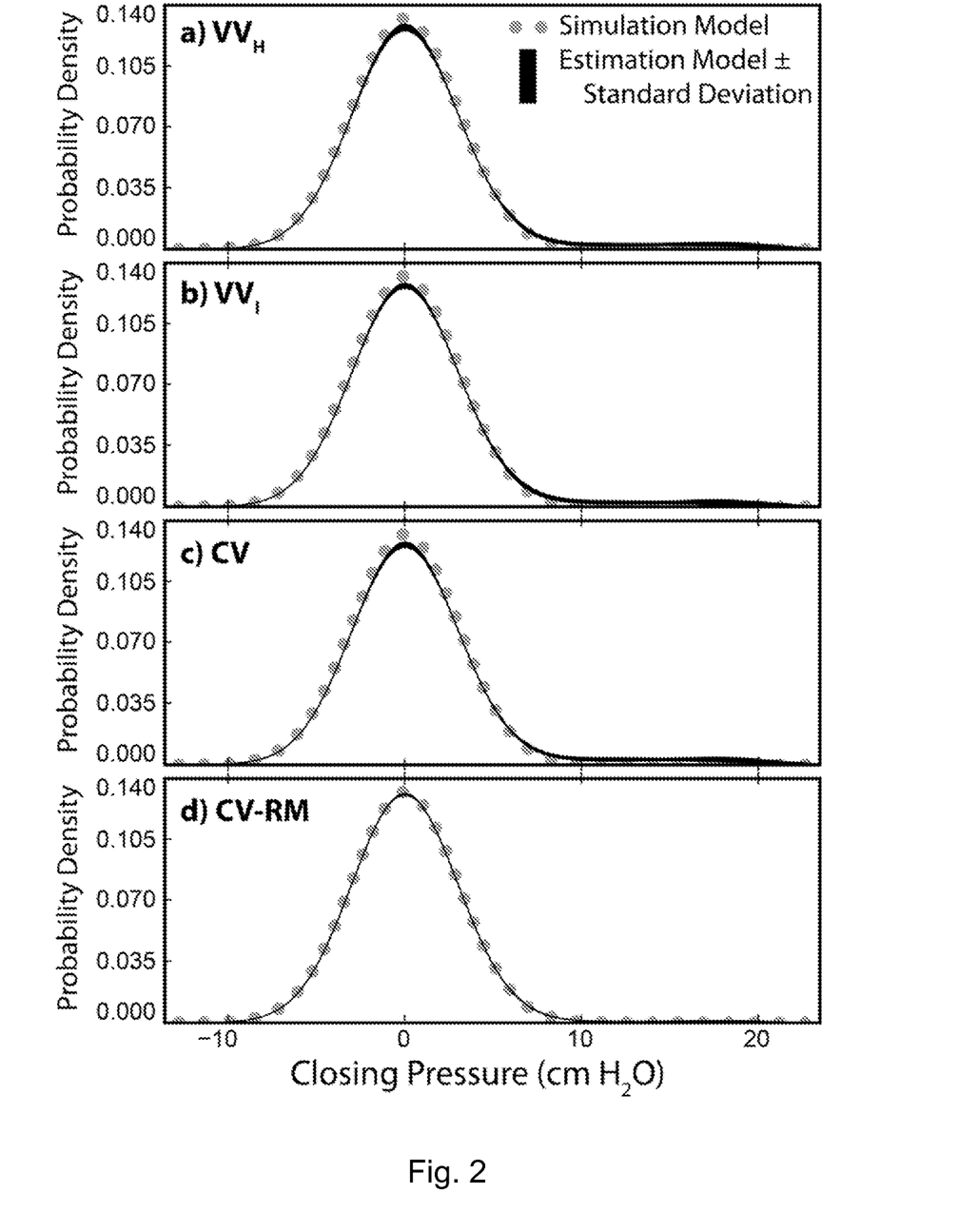
FIG. 2 plots probability density of $P_C$ for healthy mice prescribed in the simulation model (circles) and the mean±standard deviation of 16 iterations of the estimation model.

The PDF for $P_C$ used for simulating data from a healthy mouse is shown in FIG. 2 (gray circles), together with the PDF produced by the estimation model, again showing good agreement. The area of the black lines in FIG. 2 represents the mean±standard deviation. Corresponding plots for the injured mouse are shown in FIG. 3, and demonstrate that the estimation model is able to recover the bimodal distribution used in the simulation model to generate the airway pressure and flow data. Note that the position of the lower peak in the PDF for $P_C$ (at 3 cm $H_2O$) does not align with positions of any of the four Gaussians comprising the composite $P_C$ distribution used in the estimation model, demonstrating the capacity of the composite distribution to estimate the PDF for $P_C$.

The accuracy of the elastance fit was quantified as $$\varepsilon_E = \frac{E_{Base}^{Est} - E_{Base}^{Sim}}{E_{Base}^{Sim}} + \frac{V_{Crit}^{Est} - V_{Crit}^{Sim}}{V_{Crit}^{Sim}}, \quad (7)$$

where superscript Sim and Est indicate the simulation and estimation models, respectively. Likewise, the accuracy of the $P_C$ fit was described by $$\varepsilon_P = \int_{-50}^{50} |\Sigma_{i=1}^4 \alpha_i \kappa_i(P_C) - K(P_C)| dP_C \quad (8)$$

where K is the $P_C$ PDF in the simulation model and $\kappa_i$ is the PDF for $P_C$ for the $i^{th}$ Gaussian distribution in the estimation model. Statistically significant differences in $\varepsilon_E$ and $\varepsilon_P$, determined using a 1-way analysis of variance (p=0.05) and Tukey's honestly significant difference criterion, are indicated with symbols in FIG. 4.

Figure 4:
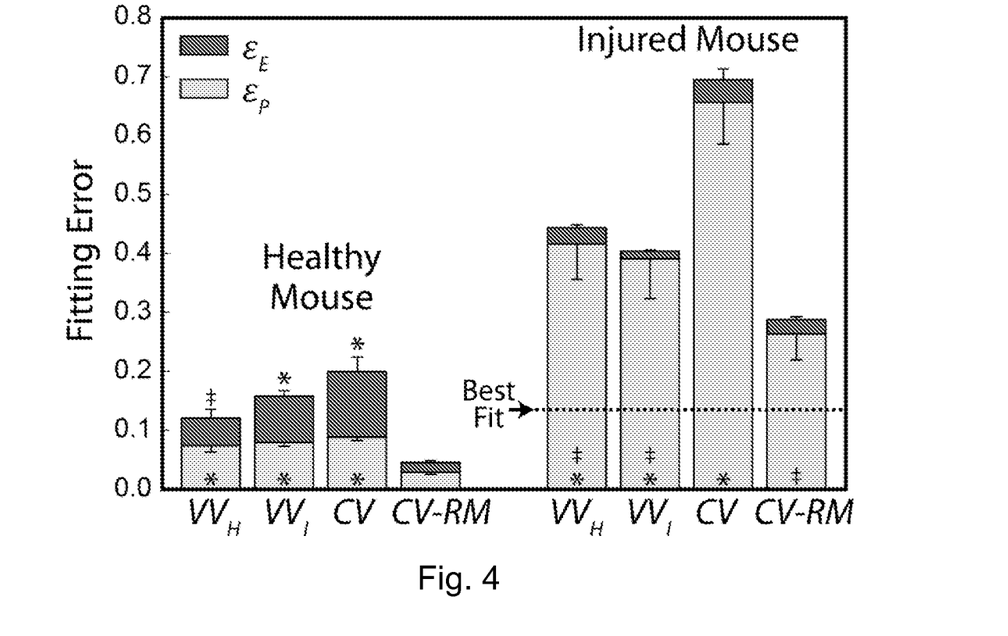
FIG. 4 shows mean error between the simulation and estimation models for 16 estimation model runs, light gray bars show error in $P_C$ and dark gray bars show errors in elastance, lines show the standard error, * indicates a significant difference from CV-RM, ‡ indicates a significant difference from CV (p=0.05), dashed line shows the lowest possible value of $\epsilon_P$ for the injured mouse due to the composite $P_C$ PDF.
Figure 5:
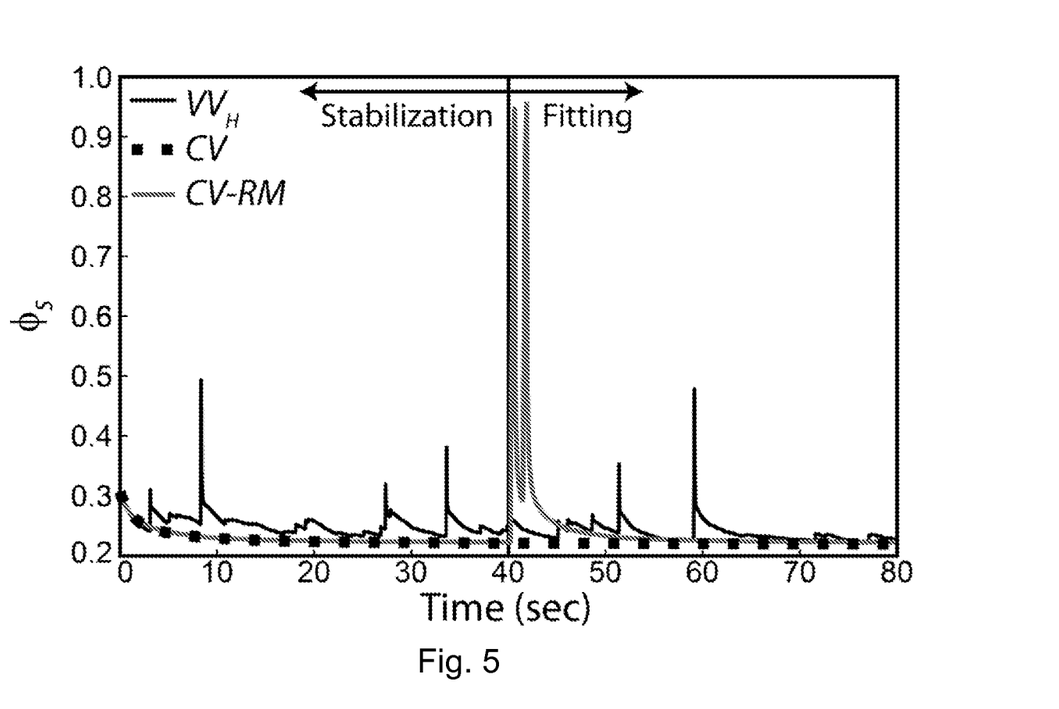
FIG. 5 plots open fraction predicted by the simulation model for an injured mouse wherein the first 40 seconds of the simulation is used to initialize the model and the second 40 seconds is used to fit the estimation model.

The performance of the estimation algorithm was proportional to the degree to which the applied ventilation waveform perturbed the model system. FIG. 5 shows that CV-RM spanned the widest range of open fractions and, as shown in FIG. 4, provided the best parameter estimate. The dashed line in this figure shows the minimum possible value for $\varepsilon_P$ due to the composite PDF used in the estimation model.

Figure 6:
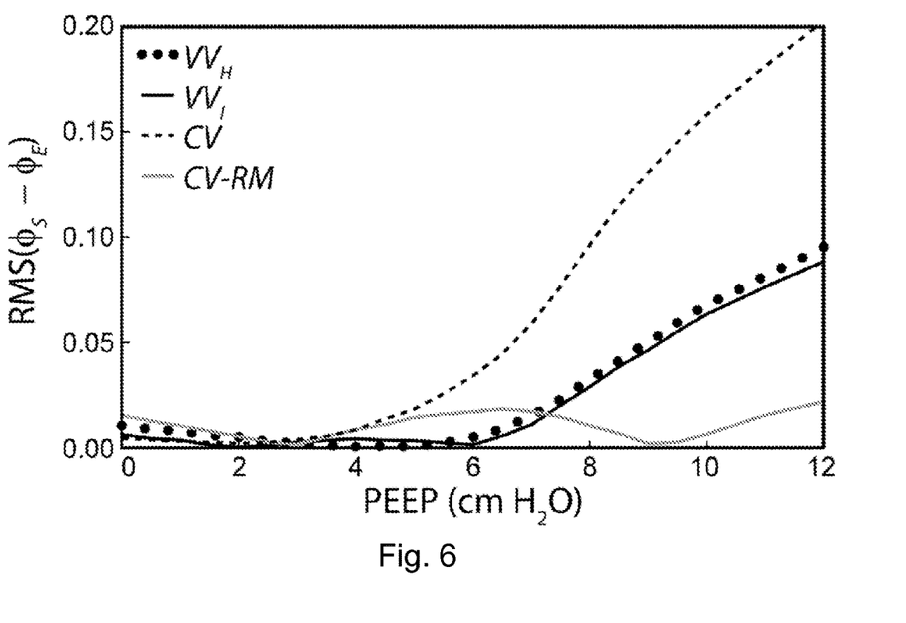
FIG. 6 plots average error in the open fraction during derecruitability tests at different PEEPs using parameters determined via the estimation algorithm and compared to the simulation model for injured mice.

To evaluate the efficacy of the fitting method in recovering data which could be used to evaluate injury or optimize mechanical ventilation, the open fraction φ during 'derecruitability tests' was determined, which was previously demonstrated are a sensitive measure of lung injury. φ was utilized to test the performance of the estimation model because changes in the open fraction of the lung that occur as a result of R/D play a role in the genesis of VILI. The derecruitability tests comprised a 1 minute stabilization period ($V_t$=0.25 ml, 200 breaths/minute) followed by a recruitment maneuver (2 breaths of $V_t$=0.25 ml, 50 breaths/minute) as described above for the simulation model. The predicted open fraction was then monitored during 3 minutes of ventilation at 8 ml/kg and 240 breaths/minute. This procedure was repeated for a range of PEEPs. The root mean square (RMS) difference in φ predicted using the average parameters determined with the estimation model ($φ_E$) and prescribed in the simulation model ($φ_S$) was used to quantify the model accuracy during the derecruitability tests. FIG. 6 shows the average RMS($φ_S$-$φ_E$) for 10 simulations of the VILI mice at ½ cm $H_2O$ PEEP increments. Here it is noted that at low PEEPS all modes of ventilation resulted in excellent approximations to the parameters used in the simulation model. However, as PEEP increased, the accuracy of the φ predictions decreased.

The pulmonary edema that characterizes ARDS impairs surfactant function and causes increased derecruitment of small airways and alveoli. This, in turn, increases the susceptibility of the lung to VILI as a result of the excessive fluid-mechanical and tissue stresses that invariably accompany mechanical ventilation. The current standard of care in ARDS is a one-size-fits-all approach employing low $V_t$ to reduce volutrauma, and is based on the reduction in mortality reported with 6 ml/kg compared to the nominal prior standard of 12 ml/kg. However, the seminal clinical trial on which the low $V_t$ approach is based employed a large number of patients at multiple sites and at huge expense. Gaining new evidence to further refine the 6 ml/kg target is probably beyond the practical limits of randomized clinical trials because of the large number of patients that would be required to obtain statistical significance.

Currently, PEEP and the fraction of inspired oxygen ($FiO_2$) are both frequently prescribed based on blood oxygenation, and thus provide some degree of personalized management aimed at optimizing the efficacy of gas exchange. However, while decrements in oxygenation are readily measured in the clinic, they lag behind the lung derecruitment that is responsible for them, suggesting that better personalized control of VILI would be achieved by monitoring lung function. In addition, lung function measurements potentially reflect the repetitive R/D events and the tissue over-distension that constitute the fundamental injurious processes behind VILI. Accordingly, further improvements in the ventilatory management of ARDS patients may use a personalized approach that adapts to the changing lung mechanics of individual patients. This approach would use continuous monitoring of lung function to adjust the parameters of a predictive computational model which is then used to determine the least injurious mode of ventilation.

In a series of previous studies in mice, it was demonstrated that the dynamics of R/D are sensitive and specific indicators of lung injury, and that they can be used to follow the progression of VILI. Accordingly, the dynamic derecruitability of the lung constitutes the appropriate readout on which to base an adaptive and personalized strategy for mechanical ventilation of the ARDS lung. In prior mouse studies, derecruitability was estimated from the transient responses in lung elastance observed during episodes of mechanical ventilation at different levels of PEEP, each episode being preceded by a large inflation to recruit closed lung units. These maneuvers provided the volume perturbations necessary for identifying the lung's propensity to derecruit, but they would almost certainly be unacceptable in the clinical arena; very large inflations may themselves cause VILI, and ventilation for even a few minutes at a low level of PEEP may be highly inadvisable for severely injured lungs because it would promote atelectrauma.

VV imposes a set of volume perturbations that is rich enough to allow accurate identification of the dynamic R/D characteristics of the lung. The extent to which this can be verified is a matter of degree; even conventional mechanical ventilation perturbs lung volume, and so should itself be able to reveal R/D dynamics to some extent. The problem with conventional ventilation, however, is that its perturbations are completely regular and rather modest, and thus can only reveal the derecruitability characteristics of the lung over a limited range of operating conditions. By contrast, the explicit goal of VV is to impose a varied volume perturbation to the lung, so it would be much better suited to the identification of lung derecruitability. Also, VV has shown potential as a therapy for ARDS in both animals and humans due to increased surfactant secretion and recruitment.

Simulated airway pressure and flow data were used to test the use of various ventilation patterns in the assessment of lung derecruitability. The data were generated by an established computational model of R/D dynamics, which allowed objective comparisons of the performances of the various ventilation patterns to be made since the true R/D characteristics represented by the data were known precisely. The ability to determine derecruitability accurately is closely linked to the range over which volume is perturbed, at least for the data from the simulated healthy mouse. Thus, for example, CV-RM gave the best estimates of the true parameter values (FIGS. 2, 3, and 4), potentially because of the very large degree of derecruitment that was induced by the initial deep inspirations in this scenario (FIG. 5). By contrast, the very limited amount of recruitment produced by CV resulted in the least accurate parameter estimates. These differences occurred because the peak pressures did not exceed approximately 10 cm $H_2O$ with CV, so the open fraction varied, on average, by less than 1% as shown in FIG. 5. Consequently, changes in $\alpha$ and $\lambda$ did not substantially impact the objective function. On the other hand, with CV-RM the airway pressures reached almost 30 cm $H_2O$ causing $\varphi$ to span from an average of 0.22 to 0.96. Therefore, even minor changes in R/D properties are reflected in the objective function obtained with CV-RM.

The two VV ventilation patterns were intermediate in performance between these two extremes, as shown in FIG. 4. The predicted open fraction for $VV_H$ in the injured mouse is shown in FIG. 5, demonstrating that a sufficient period of low $V_t$ ventilation must follow a deep breath for derecruitment to occur and provide information for the parameter fitting. The timing between these recruitment events is implicit in the definition of the VV tidal volume PDF (Eq. 4). Interestingly, all four ventilation patterns provided good estimates of the nonlinear elastance for the injured mouse simulations. This was likely due to the fact that all the ventilation patterns perturbed lung volume enough to cause $V_{Unit}$ to exceed $V_{Crit}$ in those lung units that remained open. In contrast, $V_{Unit}$ did not exceed $V_{Crit}$ during CV and $VV_I$ in the healthy mouse simulations due to the greater degree of recruitment.

The accuracy of the estimation model was further assessed by simulating derecruitability tests in injured mice over a range of PEEP using the best-fit parameters. At low PEEP, there were only minor differences in $\varphi$ between the estimation and simulation models (FIG. 6), as expected due to the good agreement in the $P_C$ distributions (FIG. 3). However, with increasing PEEP, the estimated $\varphi$ diverged progressively from that of the simulation model for all ventilation modes except CV-RM (FIG. 6). This deviation at high PEEP is proportional to the peak pressures during the fitting period and is also reflected in the pressure and elastance errors (FIG. 4). These findings demonstrate the tradeoff between the ability of a ventilation mode to avoid damaging the lung (i.e., not causing large volume excursions) versus providing the information necessary to assess derecruitability. On balance, VV achieves a useful compromise between these competing factors.

The real-world efficacy of the parameter estimation algorithm could be impaired by noise in the measured pressure response to a prescribed flow. The results of the estimation model were compared in the absence and presence of random noise in the pressure signal using $VV_I$ in an injured mouse. The noise in $P_{sim}$ was drawn from a Gaussian distribution with a standard deviation of 0.22 cm $H_2O$, equal to 1% of the peak-to-peak pressure amplitude. Eight iterations of the estimation algorithm were evaluated, for each iteration the initial conditions were identical in the noisy and noise-free cases. The addition of noise did not significantly change the mean of the fitted values for $\alpha$, $\lambda$, $E_{Base}$ or $V_{Crit}$ (paired t-test, p=0.01). However, the mean standard deviation of the predicted parameter values did increase by 53%. These findings suggest that the estimation algorithm is robust enough to provide accurate parameter estimates in the presence of noise.

In summary, a numerical optimization algorithm was developed that uses pressures and flows evaluated at the trachea to identify a distributed model of the lung that encompasses its intrinsic stiffness as well as the dynamics of R/D. The performance of this algorithm was evaluated using simulated data representing healthy and injured mice subjected to four types of mechanical ventilation. Results indicate that the spectrum of lung volume perturbations provided by VV is rich enough for the ongoing assessment of lung derecruitability. This potentially gives VV a useful diagnostic capability to complement its emerging role as a therapeutic modality.

In one embodiment, mechanical ventilation may assess the injury status of a lung, predict how much VILI will be caused in that lung by a given regimen of mechanical ventilation, and optimize ventilation to be minimally injurious based on the information from the assessment and prediction. These three steps may be cycled through continuously.

The assessment of the current state of injury to the lung may be measured using certain aspects of the lung's dynamic mechanical behavior. By tracking the transient changes in lung impedance that occur following perturbations in the magnitude of $V_t$, the lung's propensity to derecruit over time can be determined, something shown to be a sensitive indicator of injury status. In mouse models of ARDS, the VV serves as a method of measuring lung derecruitability in a clinically acceptable manner.

Computational models, such as those disclosed herein, can predict the amount of VILI that will be produced by a given regimen of mechanical ventilation. A computational model of the lung incorporates explicit representations of how volutrauma and atelectrauma injure the lung epithelial barrier, leading to a positive feedback loop of fluid and protein leak into the airspaces followed by worsening injury.

Search algorithms can be used to optimize the ventilation regimen for a given lung. Efficient numerical search algorithms can find minimally injurious ventilation strategies predicted by the computational model of lung mechanics and injury development.

The closed-loop control of mechanical ventilation in ARDS may require virtually immediate feedback on the current injury status of the lung. Feedback may also need to be continual; whatever is being measured may need to be available on an ongoing basis for an indefinite period of time. These requirements may preclude the use of conventional biomarkers of injury such as inflammatory cytokines and bronchoalveolar lavage contents, as well as blood gases, measures derived from tissue samples, and x-ray imaging, leaving parameters of lung mechanics as potentially the only suitable candidates. Lung mechanics can be tracked throughout time from ongoing measurements of pressure and flow at the airway opening if the patient is ventilated passively, meaning there are no spontaneous breathing efforts. In the case of a patient on partial ventilator support, it may be necessary either to measure transpulmonary pressure with the aid of an esophageal balloon or to apply the forced oscillation technique at the tracheal opening at oscillation frequencies well above those contained in the ventilator waveform. Thus, the closed-loop control can be used with passive ventilation, partial ventilation support, or esophageal balloons.

Figure 7:
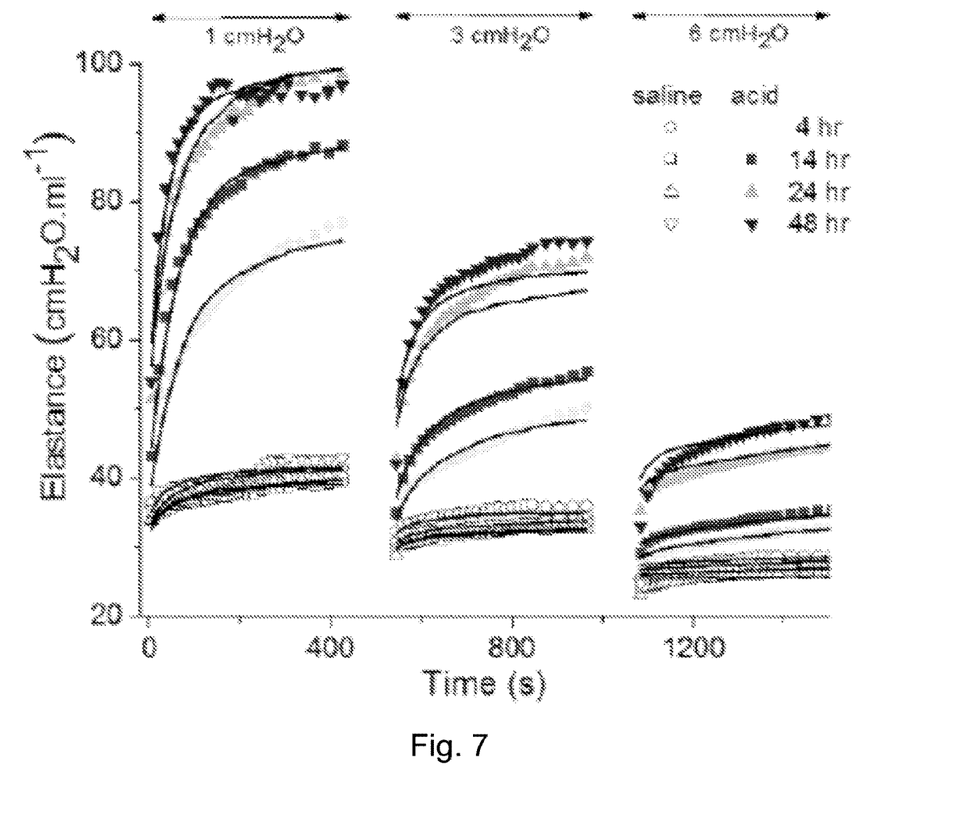
FIG. 7 compares lung elastance versus time during regular mechanical ventilation (Vt=0.2 ml) followed by a recruitment maneuver in normal (saline instilled) mice (open symbols) and in mice treated with an intra-tracheal installation of hydrochloric acid (closed symbols) at PEEP levels of 1, 3, and 6 cmH$_2$O, wherein the solid lines are the fits to the data at all three PEEP levels simultaneously by the computational model of R/D dynamics.

The injury status of the lung is most readily reflected in derecruitability, which can be determined by observing the transient increases in lung elastance that occur in the minutes following a recruitment maneuver (FIG. 7). The rate and magnitude of the elastance increases, and their dependencies on PEEP, are sensitive indicators of the degree and nature of lung injury. Furthermore, the data obtained from these maneuvers can be fit to a computational model of lung R/D dynamics that provides an assessment of derangements in surfactant function. Finally, the injuries wrought by mechanical ventilation are inherently mechanical in nature. It thus follows that the source of the feedback information required to optimally control mechanical ventilation in ARDS can be found in appropriate measurements of lung mechanics.

One problem is that characterizing derecruitability in the lung requires that lung volume be perturbed periodically, so that its dynamic response to such perturbations can be recorded. This has been achieved in mouse models of lung injury by inflating the lung briefly to total lung capacity, recording elastance over the following few minutes of regular ventilation, and then repeating this procedure at PEEP levels ranging from 1 to 6 cm $H_2O$. While this provides the necessary data to characterize the lung's propensity to derecruit over time, it is not a procedure that may be best for ARDS patients because it could damage to an already injured lung. A method of regularly perturbing lung volume in a way that is safe for an ARDS patient while still enabling identification of the dynamics of R/D may be used.

Figure 8:
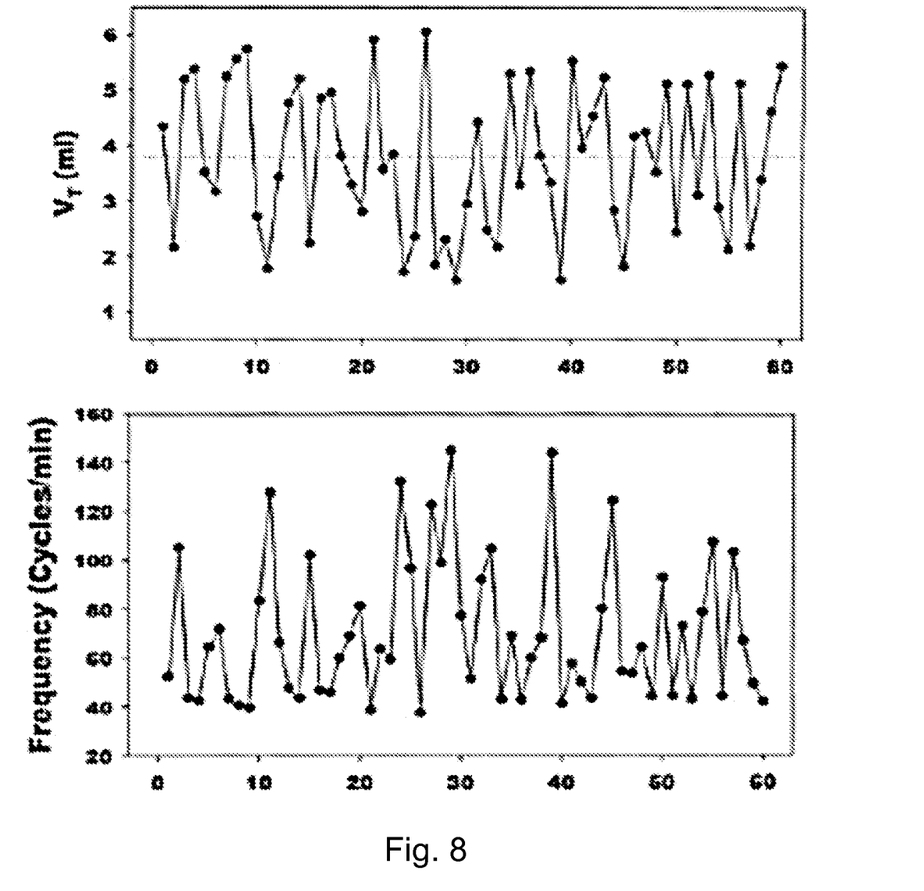
FIG. 8 illustrates example segments of VV applied to mice.

VV may be used to identify the dynamics of R/D. VV is a new mode of ventilation that employs breath-by-breath variations in $V_t$ and frequency (as in FIG. 8), and which has been shown to be protective compared to regular ventilation at the same mean $V_t$. The efficacy of VV is thought to be related to the fact that it mimics the variability of natural ventilation. This variability can serve as a system identification tool. In other words, VV may be both therapeutic and diagnostic at the same time. VV has been applied to a computational model of the injured lung, showing that the resulting airway pressure-flow relationships can be used to recover distributions of parameters that define how the lung recruits and derecruits as a function of both time and pressure.

In a number of studies of mouse models of ARDS and VILI, it has been shown that recruitment and derecruitment in the lung are phenomena that take time to manifest. They do not occur immediately upon a change in airway pressure, but rather develop over time at a rate that is strongly influenced by the type and degree of lung injury. This phenomenon can be demonstrated by assessing what is the derecruitability of the lung. This is done by applying a recruitment maneuver (a large breath approaching total lung capacity) to a mouse in order to open closed lung regions, and then ventilating the animal with a modest $V_t$ for the following 3-5 minutes while lung elastance is measured every 15 seconds. This procedure is repeated at three different levels of PEEP (1, 3 and 6 cm $H_2O$). Elastance increases progressively with time as the lung progressively derecruits. This increase in elastance is markedly diminished as PEEP increases and is markedly accentuated when the lung is injured (FIG. 7).

One embodiment uses a computational model of the lung capable of accurately recapitulating the dynamics of lung R/D. The model is comprised of numerous parallel elastic units, each served by an airway that can close with a latency that depends on the pressure (P) applied to it relative to a critical opening or closing pressure ($P_o$ and $P_c$ respectively). The time taken for an airway to open or close is proportional to how much P is above $P_o$, or how much it is below $P_c$, the respective constants of proportionality being $s_o$ and $s_c$. The behavior of the entire model is thus governed by how $P_o$, $P_c$, $s_o$ and $s_c$, are distributed across the model. This model can produce realistic dynamic pressure-volume behavior representing both normal and injured lungs when volume cycled over the vital capacity range.

This model can also be fit to lung elastance data collected during a test of derecruitability by finding distributions for $P_o$, $P_c$, $s_o$ and $s_c$ that cause the model to accurately match the measured experimental data. Gaussian distributions for $P_o$ and $P_c$ and hyperbolic distributions for $s_o$ and $s_c$ produce fits to derecruitability data from BALB/c mice injured with an intra-tracheal instillation of hydrochloric acid (FIG. 7). The effect of acid injury on the model fit increased the means of the Gaussian distributions for $P_o$ and $P_c$, something that may be indicative of impaired surfactant function leading to increased surface tension in the lungs. R/D are time-dependent phenomena, and the distributed behavior can be captured in a model that has the ability to predict how the overall mechanical properties of the lung change in time following changes in the pattern of mechanical ventilation.

Figure 9:
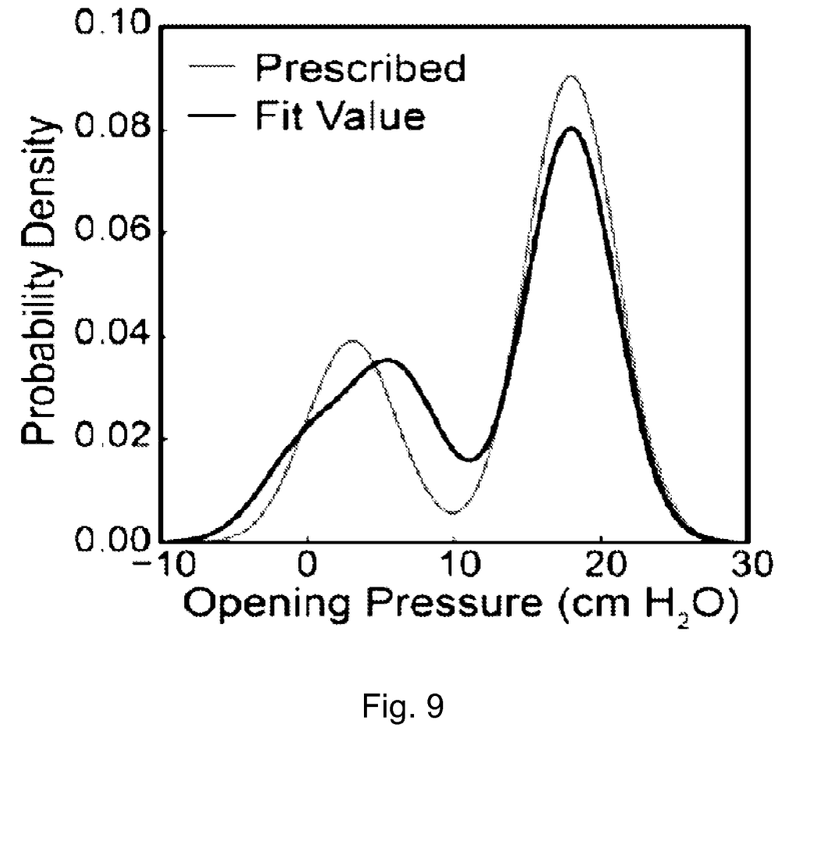
FIG. 9 compares the "true" distribution of critical opening pressures used in the computational model (thin line) and the distribution determined by fitting a reduced-order model (using parallel pattern search optimization algorithm) to airway pressure and flow data generated by ventilating the model with VV (thick line)

Efficacy of VV is likely related to the time-dependence of R/D. This relationship is exploited in reverse by using VV to infer the time dependent nature of R/D. The parameter distributions of the computational model of R/D were set to correspond to either a normal or an injured lung. Each model was subjected to a period of VV. The pressure and flow signals simulated by the model were then fit with a reduced R/D model, which used a coarse-grained set of parameter distribution functions that were scaled in the fitting procedure so as to have the fitted model predictions match the original simulation pressure-flow data as closely as possible. FIG. 9 shows the true model distribution of critical opening pressures and the estimated distribution obtained using the reduced model, and demonstrates the ability to use VV to recover key physiological features of the lung that determine its derecruitability.

Although the present invention has been described with respect to one or more particular embodiments, it will be understood that other embodiments of the present disclosure may be made without departing from the scope of the present disclosure. Hence, the present disclosure is deemed limited only by the appended claims and the reasonable interpretation thereof.

What is claimed is:

1. A method for measuring lung function of an individual being mechanically ventilated with a ventilator, comprising the steps of:

supplying, using the ventilator, a plurality of breath cycles to the individual, the breath cycles having varying tidal volumes such that at least one of the breath cycles does not have a same tidal volume as at least one of the other breath cycles;

measuring airway pressure and airway flow during the breath cycles; and determining lung derecruitability from the airway pressure measurements and airway flow measurements.

2. The method of claim 1, wherein a mean tidal volume of the plurality of breath cycles is $Vt_{Mean}$.

3. The method of claim 2, wherein the tidal volumes of the plurality of breath cycles vary from $0.7\ Vt_{Mean}$ to $2.25\ Vt_{Mean}$.

4. The method of claim 2, wherein the tidal volumes of the plurality of breath cycles vary from $0.7\ Vt_{Mean}$ to $3.5\ Vt_{Mean}$.

5. The method of claim 4, where the tidal volumes are distributed according to a specified probability distribution function.

6. The method of claim 3, where the tidal volumes are distributed according to a specified probability distribution function.

7. The method of claim 6, where the tidal volumes are distributed according to a Gaussian function.

8. An apparatus for determining a lung function of individual being ventilated by a ventilator, the ventilator configured to provide variable ventilation to the individual through an airway, the apparatus comprising:

a processor; and an airway meter in communication with the processor, the airway meter configured to measure a pressure and flow of the airway;

wherein the processor is programmed to:

receive a plurality of measurements of airway pressures and airway flows from the airway meter, wherein the plurality of measurements correspond to a plurality of breath cycles having varying tidal volume and/or breathing frequency; and determine lung derecruitability from the airway pressure measurements and airway flow measurements.

9. The apparatus of claim 8, further comprising an interface in communication with the processor, the interface configured to communicate with the ventilator.

10. The apparatus of claim 9, wherein the processor is further programmed to utilize data received from the ventilator in determining lung derecruitability.

11. An apparatus for determining a lung function of an individual, comprising:

a ventilator, the ventilator configured to provide variable ventilation to the individual through an airway;

an airway meter configured to measure a pressure and flow of the airway; and a processor;

wherein the processor is programmed to:

receive a plurality of measurements of the airway pressures and airway flows from the airway meter;

receive data from the ventilator; and determine lung derecruitability from the airway pressure measurements, airway flow measurements, and ventilator data.

\* \* \* \* \*